United States Patent [19]
Lareau et al.

[11] Patent Number: 5,767,410
[45] Date of Patent: Jun. 16, 1998

[54] LAMB WAVE ULTRASONIC PROBE FOR CRACK DETECTION AND MEASUREMENT IN THIN-WALLED TUBING

[75] Inventors: John P. Lareau, Granby; Mark V. Brook, West Hartford, both of Conn.

[73] Assignee: Combustion Engineering, Inc., Windsor, Conn.

[21] Appl. No.: 665,445

[22] Filed: Jun. 18, 1996

Related U.S. Application Data

[60] Provisional application No. 60/013,973 Mar. 19, 1996.
[51] Int. Cl.$^6$ ............................ G01N 29/10; G01N 29/26
[52] U.S. Cl. ............................ 73/623; 73/644; 376/245; 376/249; 376/252; 976/DIG. 214
[58] Field of Search ............................ 73/620, 622, 623, 73/624, 626, 628, 629, 634, 640, 641, 643, 644; 976/DIG. 214; 376/245, 249, 252

[56] References Cited

U.S. PATENT DOCUMENTS

| | | | |
|---|---|---|---|
| 4,092,868 | 6/1978 | Thompson et al. | 73/638 |
| 4,597,294 | 7/1986 | Brill, III et al. | |
| 4,691,572 | 9/1987 | van den Berg et al. | 73/643 |
| 5,062,300 | 11/1991 | Vallee | 73/623 |
| 5,256,966 | 10/1993 | Edwards. | |
| 5,267,481 | 12/1993 | Smith | 73/623 |
| 5,396,800 | 3/1995 | Drinon et al. | 73/623 |
| 5,454,267 | 10/1995 | Moreau et al. | 73/623 |

FOREIGN PATENT DOCUMENTS

| | | |
|---|---|---|
| 0 105 418 | 4/1984 | European Pat. Off. . |
| 0 301 906 | 2/1989 | European Pat. Off. . |
| 0 304 053 | 2/1989 | European Pat. Off. . |
| 0 318 387 | 5/1989 | European Pat. Off. . |
| 0 484 229 | 5/1992 | European Pat. Off. . |
| 2 702 840 | 9/1994 | France . |
| 31 31 883 | 3/1983 | Germany . |

OTHER PUBLICATIONS

Non-Destructive Testing, Second Edition; R. Halmshaw; 1991; pp. 185–187.

Silk, M.G., et al., "The Propagation in Metal Tubing of Ultrasonic Wave Modes Equivalent to Lamb Waves," Ultrasonics, Jan. 1979.

Ditri, J. J., "A Novel Guided Ultrasonic Wave Technique for Improved Tubing Inspection Efficiency", Proceedings of the 11th Conference on NDE in the Nuclear and Pressure Vessel Industries, 30 Apr.–2 May 1992.

Brook, Mark V., et al., "Ultrasonic Inspection of Steam Generator Tubing by Cylindrical Guided Waves", Review of Progress in Quantitative Nondestructive Evaluation, vol. 9, 1990.

Primary Examiner—Hezron E. Williams
Assistant Examiner—Rose M. Miller
Attorney, Agent, or Firm—Ronald P. Kananen; John H. Mulholland

[57] ABSTRACT

A probe inspects steam generator tubing for defects. The probe includes a transducer which generates a localized ultrasonic Lamb wave. The ultrasonic wave is transferred to the tubing by a coupling medium, such as water, that physically couples the transducer and the tubing. Defects in the tubing reflect the ultrasonic wave to the probe which detects the reflections. The results are then used to determine the length and depth of such defects as cracks, pitting, and thinning. The localized ultrasonic wave performs an inspection sensitive enough to detect ligaments between crack segments. This allows highly accurate predictions of tubing integrity and rupture strength.

20 Claims, 6 Drawing Sheets

FIG. 6

Theoretical calculations for lamb waves which can be generated in a steam generator tube of 0.750" diameter and 0.048" wall thickness

| Mode | Frequency Mhz | Phase Velocity mm/nsec | Group Velocity mm/nsec | Incident Angle, degrees | |
|---|---|---|---|---|---|
| | | | | Immersion | Contact |
| $A_0$ | 1.0 | 2.239 | 3.049 | 41.10 | 81.04 |
| | 5.0 | 2.733 | 2.771 | 33.06 | 81.04 |
| $S_0$ | 1.0 | 5.018 | 4.820 | 17.26 | 32.55 |
| | 5.0 | 2.836 | 2.746 | 31.62 | 72.15 |
| $A_1$ | 1.0 | --- | --- | --- | --- |
| | 5.0 | 3.662 | 2.189 | 23.16 | 47.51 |
| $S_1$ | 1.0 | --- | --- | --- | --- |
| | 5.0 | 5.167 | 3.502 | 16.44 | 31.53 |
| $A_2$ | 1.0 | --- | --- | --- | --- |
| | 5.0 | 6.834 | 2.247 | 11.34 | 23.27 |

LAMB WAVE ULTRASONIC PROBE FOR CRACK DETECTION AND MEASUREMENT IN THIN-WALLED TUBING

This application claims the benefit of U.S. Provisional application No. 60/013,973, filed Mar. 19, 1996.

BACKGROUND OF THE INVENTION

This invention relates to a rotatable probe for inspecting damage to steam generator tubing. The rotatable probe generates ultrasonic waves that are propagated in the tubing and reflected by any cracks, holes, or other structural defects affecting the integrity of the tubing. The ultrasonic wave mode used is commonly referred to as Lamb waves or the cylindrical geometric equivalent of Lamb waves. The reflected waves are detected by the probe and used to identify the location and extent of the defects.

An example of thin-walled tubing is steam generator tubing. Steam generator tubing is used in a variety of systems that translate heat energy into mechanical energy using steam. For example, in a nuclear power plant, the heat generated by a nuclear reaction is used to boil water into steam. The steam is then transmitted through piping to turbines. The steam pressure then drives the turbines to generate electricity. As a result, steam generator tubing is exposed to extreme operating conditions and is susceptible to stress-corrosion cracking, primary water stress-corrosion cracking, mechanical wear, thinning and pitting.

To address this susceptibility, a number of techniques have been developed commonly using a variety of eddy current non-destructive techniques and probes to inspect steam generator tubing for degradation prior to tube failure in order to prevent forced outages. Steam generator tubing has been most commonly inspected using a variety of eddy current methods. Except for the bobbin probe, almost all other probes contain spot coils requiring that the probe be rotated or contain multiple coils in an array probe to provide complete circumferential coverage of the tube wall, along with axial translation.

An example of a nondestructive tubing inspection system is taught in U.S. Pat. No. 4,597,294, while an example employing a bank of coils is taught in U.S. Pat. No. 5,256,966. The different probe designs of the prior art, whether rotating probes or array probes, are aimed at examining regions of special interest in the tubing, and to confirm ambiguous bobbin probe indications. Substantially all eddy current probes are sensitive to tube diameter changes caused by expansion transitions, dents, U-bends, and sludge deposition.

In the generalized eddy current method, a probe is axially inserted into the tubing. The probe is in proximity with the side of the tubing and induces an electrical current into the tubing. As the current flows through the surrounding area of the tubing, eddy currents will be affected by the presence of any defect. The probe then detects the eddy currents from which the size and nature of the tubing defect can be determined.

A principal problem with the eddy current probe is the time required to inspect the tubing. The probe can only effectively evaluate a very small area of the tubing wall at a time at a particular axial location. The probe must then be rotated to evaluate the neighboring portion of the tubing wall. Rotation continues until the entire circumference of the tube has been inspected. The probe is then further inserted along the axis of the tube to inspect another circumferential portion. This continues until the entire portion of the tube requiring inspection has been tested and, if desired, mapped by scanning techniques.

Though highly accurate, the eddy current method of inspecting steam generator tubing is relatively slow and expensive. Accordingly, there have been a number of attempts to use Lamb wave techniques for inspection of steam generator tubing. For example, M. G. Silk and K. F. Bainton, "The Propagation in Metal Tubing of Ultrasonic Wave Modes Equivalent to Lamb Waves", Ultrasonics (January 1979) reports investigations of the generation of ultrasonic wave modes in thin-walled metal tubing with piezoelectric ultrasonic probes. M. V. Brook, T. D. K. Ngoc, and J. E. Eder, "Ultrasonic Inspection of Steam Generator Tubing by Cylindrical Guided Waves", Review of Progress in Quantitative Nondestructive Evaluation, Vol. 9, pp. 243 to 249 (Plenum Press 1990) also discusses using cylindrical guided waves (CGW) for inspection of steam generator tubing (SGT). J. J. Ditri, J. L. Rose, F. T. Carr and W. J. McKnight, "A Novel Guided Ultrasonic Wave Technique for Improved Tubing Inspection Efficiency" Proceedings of the 11th International Conference on NDE in the Nuclear and Pressure Vessel Industries, Apr. 30 to May 2, 1992, pp. 49 to 54 explores the utility of guided ultrasonic waves for increasing the efficiency and sensitivity of nuclear steam generator tubing. In general, the Lamb ultrasonic wave method of inspection was useful to supplement the eddy current method.

A main advantage of the Lamb wave method is that it is not a "spot" technique for tubing inspection. Using Lamb waves, a defect can be detected at relatively long distances from the probe. The range of an ultrasonic Lamb wave probe depends on the wave mode and frequency selected, the information about the defect sought, and the probe design used.

The ultrasonic Lamb wave method is made possible because the attenuation of Lamb waves is exceptionally low. The Lamb waves can propagate for a relatively long distance without losing much energy. Lamb waves of a typical amplitude can still be readily detected after traveling a distance of about 10 meters. Another important feature is that Lamb wave propagation is not sensitive to relatively smooth changes in the tubing diameter or tube bend, such as expansion transition, dents and U-bends.

A prototype ultrasonic Lamb wave probe 13, as shown in FIG. 1, consists of an annular or conically shaped piezoelectric element 11, which acts as a transducer; and a coupling medium 15 delivered by a medium flow line 12. The medium physically couples the transducer element 11 and the inner surface of the tube 14. This allows the Lamb waves to be conducted from the transducer and excited in the tubing at a certain incident angle. The intention of such probe design is to generate the radially symmetric Lamb waves that are used to inspect the tube. Thus, the entire circumference of the tube is covered by a single axially propagating wave front.

Another similar approach also known in the prior art is shown in FIG. 2. This probe 20 makes use of a flat piezoelectric crystal 26 which is coupled by a coupling medium 28 to a conical wave reflector 29 which creates a single axially propagating wave front which covers the entire circumference of the tube 27. The flat crystal 26 and the wave reflector 29 shown in FIG. 2 function similarly to the conical crystal shown in FIG. 1.

Essentially all previous designs featured the use of Lamb waves that covered the entire circumference of the tube with an axially propagating wave front. The reason for this approach was to provide rapid detection of flaws without requiring the mechanically difficult and slow process of rotating a probe head to provide complete coverage with a localized beam covering only a small portion of the circumference. However, a problem with the ultrasonic Lamb wave probes previously developed is that Lamb wave probes can only indicate the location of a defect along the tubing. Characterizing the flaw by circumferential length and depth requires a different technique and probe design.

Accordingly, the need exists to improve existing Lamb wave probes to provide improved sensitivity by way of increased power density of the sound field and to provide high resolution measurements of the crack length along with discrimination of intermittent ligaments between short crack segments. Prior attempts in the art were physically incapable of measuring crack length or detecting ligaments between cracks. Yet, the most recent experience with steam generator tube cracks clearly shows that the crack length and existence of ligaments are essential factors in predicting tube rupture strength.

BRIEF SUMMARY OF THE INVENTION

It is an object of the present invention to provide an ultrasonic Lamb wave probe which makes use of localized, as opposed to circumferential, Lamb waves to make sensitive inspections of the tubing walls. The method and probe which, though slower than conventional ultrasonic Lamb wave probes, will be sensitive enough to detect circumferential cracks having a magnitude of less than 10% of the tube wall, whether located on the inside or the outside surface of the tube.

It is a further object of the present invention to provide an ultrasonic Lamb wave probe which, in conjunction with a suitable ultrasonic imaging system, can provide high resolution measurements of the crack length along with discrimination of intermittent ligaments between short crack segments. The most recent experience with steam generator tubing shows that the crack length and the existence of ligaments are essential factors in predicting the tubing rupture tolerance.

It is still another overall object of this invention to provide a method and apparatus for use of localized Lamb waves for the detection and length measurement of cracking in steam generator tubing.

It is another overall object of this invention to provide an internal probe device for introducing localized Lamb waves into a steam generator tube for propagation in either an axial or a circumferential direction.

In contrast to the state of the prior art discussed above, this invention specifically uses a localized ultrasonic beam that requires rotation for coverage of the steam generator tubing. An advantage of this technique is to provide improved sensitivity by way of increased power density of the sound field and to provide high resolution measurements of the crack length along with discrimination of intermittent ligaments between short crack segments. Prior attempts were physically incapable of measuring crack length or detecting ligaments between cracks.

A second feature of the invention is that the method and apparatus provide detection and measurement of axial cracking through a related design for propagating the wave circumferentially around a tube at a given axial location. Such a probe is translated along the tube length to provide inspection coverage. Such a probe provides for detection of axial cracking, especially in the presence of denting, which interferes with the more commonly used eddy current methods for this application.

With either axial or circumferential probe designs, the probe can incorporate an eddy current sensor to provide both ET and UT inspection coverage simultaneously. The combination of ET and UT has been done by others, but not with Lamb wave techniques, insofar as is known by the inventors. At the same time, detection and characterization of a crack will be performed some distance from the crack location which is essential for detecting cracks in deformed portions, e.g., expansions or bends, of the tubing.

In a first aspect, the invention relates to an ultrasonic probe for inspecting the integrity of steam generator tubing comprising a transducer for generating a localized ultrasonic wave; a coupling medium for transmitting the wave from said transducer to the tubing; means for detecting the reflection of said wave caused by defects in said tubing; and means for rotating said probe to provide full circumferential inspection of said tubing.

Preferably, the transducer is a piezoelectric crystal, and the localized ultrasonic wave is a Lamb wave. A multiplicity of symmetric and asymmetric Lamb wave modes may be used, for example, with a frequency of about 1 to about 5 MHz wherein the mode of the ultrasonic Lam wave is either $S_0$ or $A_1$. Means are also provided for continuously providing the coupling medium, which preferably is water.

The apparatus further includes means for using the detected reflection of the localized ultrasonic Lamb wave to determine the size and nature of defects in the tubing including ligaments between crack segments.

In a second aspect, the invention relates to a method of using ultrasonic waves to determine the integrity of steam generator tubing comprising the steps of generating a localized ultrasonic wave; transmitting the wave to the tubing; detecting the reflection of the localized wave caused by defects in said tubing; and rotating the direction of the localized ultrasonic wave to provide full circumferential inspection of said tubing.

The localized ultrasonic wave is a Lamb wave. By way of an example, a multiplicity of symmetric and asymmetric Lamb wave modes may be used with a frequency of about 1.0 to about 15.0 MHz and preferably 1.0 to about 8.0 MHz. The method includes a step of continuously providing the coupling medium which preferably is water. Preferably, the localized ultrasonic wave is generated with a piezoelectric crystal.

The method further comprises a step of using the detected reflections of said ultrasonic wave to determine the size and nature of defects in the tubing including ligaments between crack segments. An important feature is that the method and apparatus of the invention provide data compatible with an imagery system which uses A, B, B' and C scans.

An additional feature of the Lamb wave probe is the ability to inspect a tube that has been previously repaired using a process called sleeving. In this process, a degraded section of a tube has a smaller sleeve tube installed and fastened near each end to produce a leak tight or leak limiting seal. Often, it is necessary to inspect a portion of the original tube that is now covered by the sleeve, and especially those portions of the tube that have been deformed as part of the sealing process. The Lamb wave probe can introduce the wave into the tube beyond the end of the sleeve region and propagate along the tube behind the sleeve.

BRIEF DESCRIPTION OF THE DRAWINGS

FIG. 6 is a table providing technical information for the various Lamb wave modes.

DETAILED DESCRIPTION OF THE INVENTION

Figure 1:
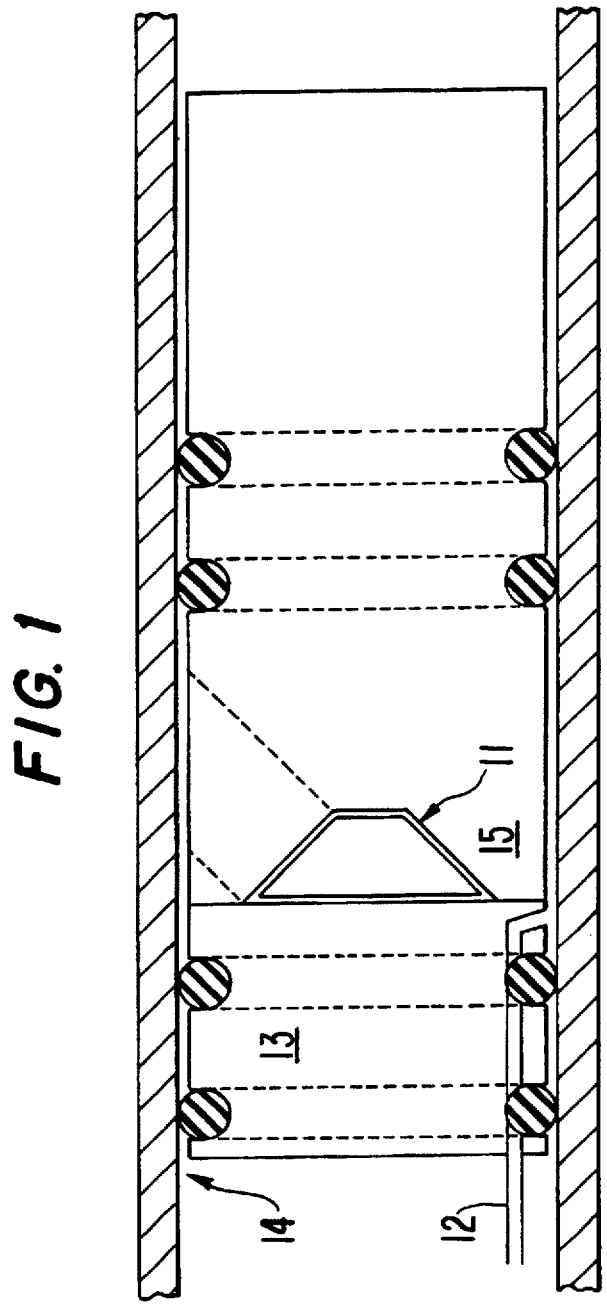
FIG. 1 is side cross-sectional pictorial representation of a conventional ultrasonic Lamb wave probe.
Figure 2:
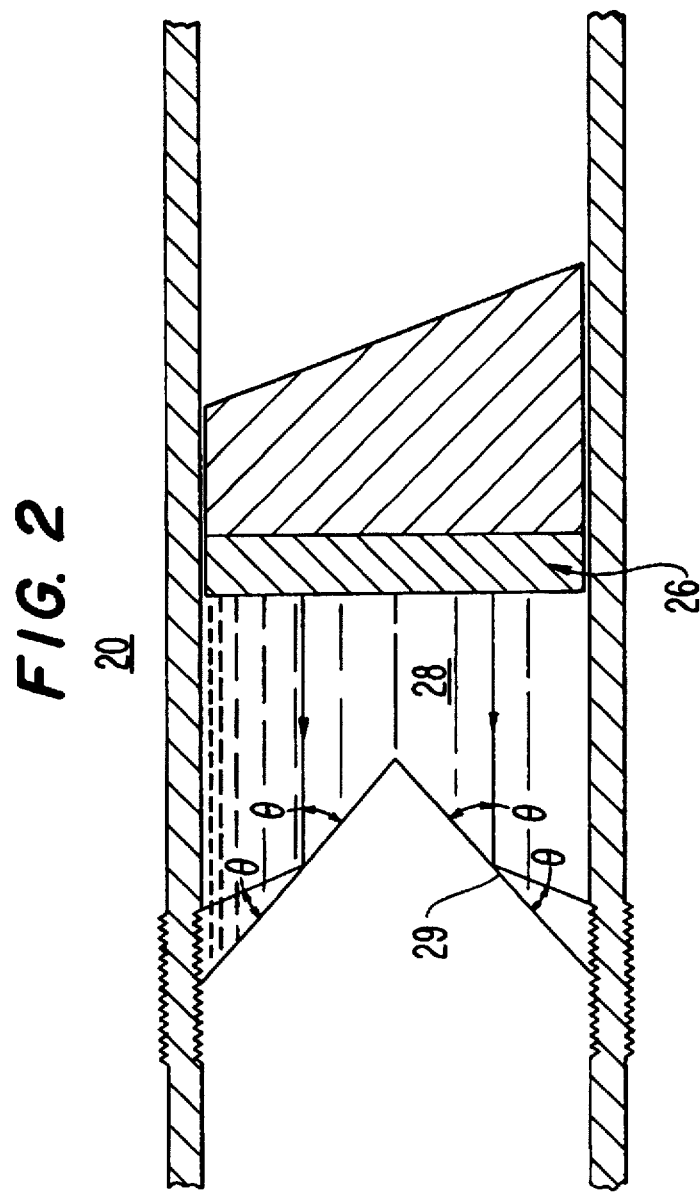
FIG. 2 is a side cross-sectional pictorial representation of another conventional ultrasonic Lamb wave probe.

According to the invention, a probe structure shown generally at reference numeral 30 is now described with reference to FIG. 3. The probe includes a probe housing 33 within which is located a transducer 31 which is generally a piezoelectric crystal. The transducer of the present invention is contrasted with the conical crystal or the flat crystal and conical reflector taught by the prior art. The transducer 31 is not designed to create an ultrasonic wave that covers the entire circumference of the tubing. Rather, the transducer 31 generates a localized wave that propagates in a desired direction in only a portion of the tubing circumference.

In order to inspect the entire tube circumference, the probe 30 must be rotated after each limited inspection is complete. By making successive rotations and inspections, the entire circumference of the tube is checked. In a test performed using the probe of the present invention, data was collected scanning circumferentially 365 degrees and digitally storing a wave form for each degree of the 360° of rotation. The probe 30 thus can then be moved to a point axially further or closer along the tubing and the process is repeated. In the test, the probe was moved forward in increments of 0.050 inches after each circumferential scan.

Though this significantly decreases the speed with which an inspection can be made in comparison to prior art full-circumference probes, the probe of the present invention is extremely accurate and represents a substantial improvement over the prior art in its ability to detect and predict steam generator tubing failure.

The wave generated by the transducer is transferred into the tubing by way of a coupling medium (not shown). This coupling medium is typically water which is pumped into the area between the transducer 31 and the tubing through a fitting 34, attached to a connector 35. Also attached to connector 35, is a coaxial cable 40 with which the probe communicates with the system. A sealing ring 36 and gasket 37 prevent water from leaking back down the tubing. Forward 38 and rear 39 centering fingers center the probe 30 within the tubing. Lamb waves, once excited in the tubing, may be made to propagate along the tubing in either a forward or backward direction as desired.

Figure 3:
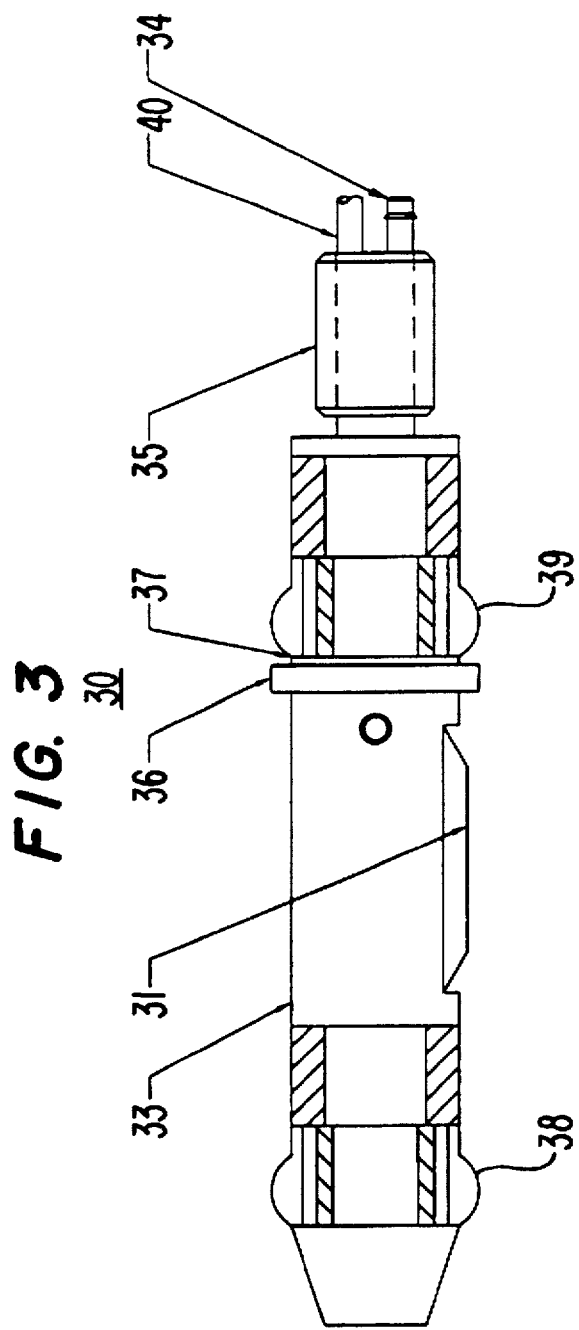
FIG. 3 is a side cross-sectional view of the ultrasonic Lamb wave probe of the present invention for circumferential crack detection.
Figure 4:
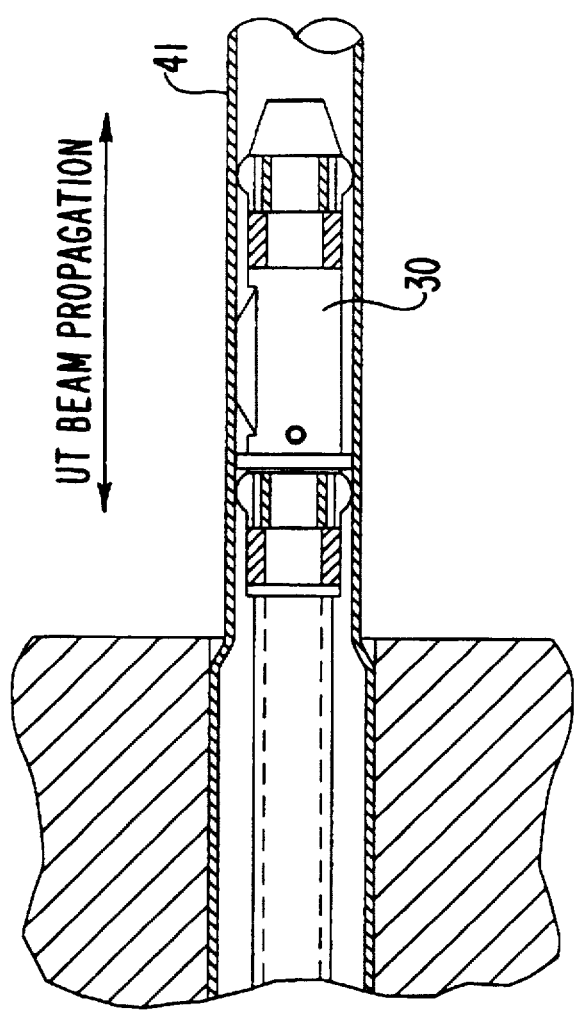
FIG. 4. shows positioning of the Lamb waves in the steam generator tubing.

FIG. 4 shows the positioning of the probe 30 of FIG. 3 in tubing 41. The arrows indicate the possible directions of Lamb waves propagation. As can be seen, the direction of propagation of the Lamb waves in the tube 41 is axial.

Figure 5:
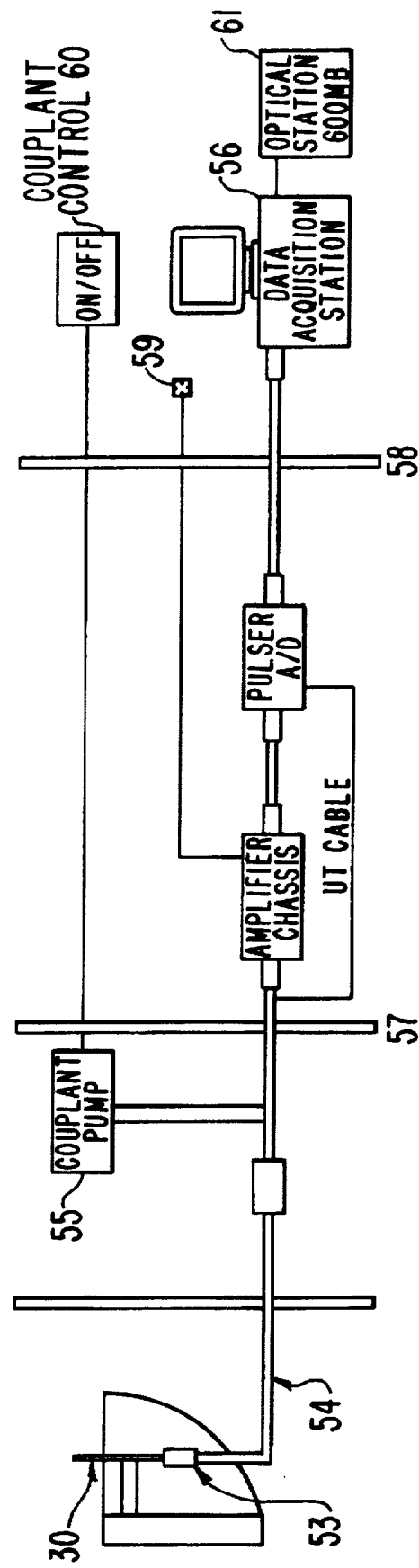
FIG. 5 is a schematic view of the entire Lamb wave probe apparatus including supporting machinery.

The entire tubing inspection system is shown in FIG. 5. The probe 30 is driven by a probe driver 53 for both rotational and translational motion. A scanner cable 54 connects the probe 30 and the probe driver 53 to the coupling medium or couplant pump 55 and a data acquisition center 56. A bio-shield 57 and containment walls 58 may be used when the steam generator tubing is in or near a hazardous environment, such as a nuclear reactor. A couplant control 60 for the couplant medium pump 55 is also provided.

A joystick 59 or other control may be provided for remote manual guidance of the probe 30 in the tubing. An optical disk 61 for data storage may also be provided.

As noted for the preferred embodiment, the medium for physically coupling the transducer and the tubing is water. However, as will be recognized by those of ordinary skill in the art, other fluids may be used as the coupling medium with varying results. Glycerol is an example.

Additionally, there are other known means of physically coupling the transducer and the tubing. These include using a solid medium to transfer the ultrasonic waves from the transducer to the tubing, or placing the transducer in direct contact with tube.

FIG. 6 shows sample calculations for Lamb waves in a steam generator tubing which is 0.048 inches thick and has a 0.750 inches diameter, five ultrasonic wave modes equivalent to Lamb waves can be generated in the frequency range from 0 to 6.0 MHz These modes are known in the art as: A0, A1, A2, S0, and S1. At a frequency of 1.0 MHz, only modes A0 and S0 can be generated. It requires a frequency of 5.0 MHz to generate all five modes.

Not all of these modes can be used for practical application. For example, at the 5.0 MHz frequency, the S1 mode produces low amplitude and wide signals. The highest signal amplitude is produced by the A1 mode, followed by the A0 and S0 modes. In contrast, at a frequency of 1.0 MHz, the A0 mode provides the best results.

We claim:

1. An ultrasonic probe for incrementally circumferentially inspecting the integrity of steam generator tubing comprising:

a transducer for generating localized ultrasonic waves propagating in a predetermined direction in only a portion of a circumference of said tubing at a first axial location;

a medium for transmitting the waves from said transducer to said portion of said tubing;

means for detecting the reflection of said waves caused by defects in said tubing in a limited inspection of said tubing at each said portion of said circumference; and means for successively incrementally rotating said probe after each limited inspection to provide full circumferential inspection of said tubing.

2. An ultrasonic probe as claimed in claim 1, wherein said transducer is a piezoelectric crystal.

3. An ultrasonic probe as claimed in claim 1, wherein said ultrasonic waves are equivalent to Lamb waves.

4. An ultrasonic probe as claimed in claim 3, wherein said ultrasonic Lamb wave is generated with a frequency in a range of about 1 to about 8 MHz.

5. An ultrasonic probe as claimed in claim 4, wherein the mode of said ultrasonic Lamb wave is any on of the first three modes.

6. An ultrasonic probe as claimed in claim 1, further comprising means for continuously providing said medium.

7. An ultrasonic probe as claimed in claim 6, wherein said medium is water.

8. An ultrasonic probe as claimed in claim 1, further comprising means for using the detected reflection of said ultrasonic wave to determine the size and nature of defects in the tubing including ligaments between crack segments.

9. The ultrasonic probe as set forth in claim 1, further including means for incrementally axially positioning said probe after each full circumferential inspection of said tubing comprising a plurality of limited circumferential inspections.

10. The ultrasonic probe as set forth in claim 1, wherein said transducer is located with a housing of said probe.

11. The ultrasonic probe as set forth in claim 1, wherein said means for successively rotating said probe incrementally successively rotates said probe at about each degree of rotation.

12. A method of using ultrasonic waves to determine the integrity of steam generator tubing comprising:

generating a localized ultrasonic wave that propagates in a predetermined direction in only a portion of the tubing circumference;

transmitting said wave to said tubing through a transmissive medium;

detecting, successively and incrementally, the reflection of said wave caused by defects in said tubing for each said portion of the tubing circumference to detect the reflection over the entire circumference of said tubing; and rotating the ultrasonic wave for each successive portion of said circumference during said detection step to provide full circumferential inspection of said tubing.

13. A method as claimed in claim 12, wherein said ultrasonic wave is a Lamb wave.

14. A method as claimed in claim 12, wherein said ultrasonic Lamb wave is generated with a frequency in a range of about 1 to about 8 MHz.

15. A method as claimed in claim 14, wherein the mode of said ultrasonic Lamb wave is any one of the first three modes.

16. A method as claimed in claim 12, wherein said medium is continuously provided.

17. A method as claimed in claim 16, wherein said medium is water.

18. A method as claimed in claim 12, wherein said ultrasonic wave is generated with a piezoelectric crystal.

19. A method as claimed in claim 12, further comprising using the detected reflections of said ultrasonic wave at each successive portion of said circumference to determine the size and nature of defects in the tubing including ligaments between crack segments.

20. A method for inspecting steam generator tubing comprising:

generating localized ultrasonic Lamb waves that propagate in a predetermined direction in the tubing structure to be inspected for each of a plurality of circumferential positions and at a first of a plurality of axial locations along said tubing;

generating said localized ultrasonic Lamb waves in the tubing structure to be inspected for each of a plurality of circumferential positions and at a second of said axial locations along said tubing; and repeatedly detecting the reflections of said localized Lamb waves to construct a scan of inspections during each of said generating steps, thus to detect flaws in said steam generator tubing.

* * * * *